United States Patent [19]
Pfannenstiel et al.

[11] Patent Number: 5,804,730
[45] Date of Patent: Sep. 8, 1998

[54] ULTRASONIC TESTING METHOD

[76] Inventors: Richard A. Pfannenstiel, 2 James Ct., Old Saybrook, Conn. 06475; Steven L. Sikorski, 101 Bushy Hill Rd., Deep River, Conn. 06417

[21] Appl. No.: 541,444

[22] Filed: Oct. 10, 1995

[51] Int. Cl.$^6$ .......................... G01N 29/06; G01N 29/10; G01N 29/24
[52] U.S. Cl. ................................................ 73/622; 73/624
[58] Field of Search ............................. 73/618, 622, 620, 73/627, 629, 624

[56] References Cited

U.S. PATENT DOCUMENTS

| | | | |
|---|---|---|---|
| 3,575,042 | 4/1971 | Lovelace et al. | 73/620 |
| 4,170,145 | 10/1979 | Kennedy et al. | 73/620 |
| 4,294,118 | 10/1981 | Shiraiwa et al. | 73/620 |
| 4,570,487 | 2/1986 | Gruber | 73/624 |
| 4,730,495 | 3/1988 | Green | 73/620 |
| 4,841,489 | 6/1989 | Ozaki et al. | 73/633 |

*Primary Examiner*—Hezron E. Williams
*Assistant Examiner*—Rose M. Miller
*Attorney, Agent, or Firm*—Robert H. Montgomery

[57] ABSTRACT

A single operation, multi-task, non-destructive testing technique of ultrasonic examination for defect detection, analysis and sizing. The technique utilizes the same angle, mode of propagation, calibration, set-up, and scanning patterns, for all materials, thickness of materials, and configuration of components for which it is applicable. The technique is used to detect, analyze and size planar flaws, such as fatigue cracks, which are connected to the surface opposite that from which the ultrasound is propagated. The technique relies on the fact that specular reflections received from flaws that have penetration into materials will return to the transducer before reflections which are associated with geometric features of the surface to which the flaw is connected. It also relies on the properties of the longitudinal mode of sound propagation at a 65–75 degree angle resulting in reduced specular reflections from opposite wall geometric reflectors such as weld roots and counterbores.

25 Claims, 3 Drawing Sheets

ULTRASONIC TESTING METHOD

FIELD OF THE INVENTION

This invention relates to ultrasonic testing of metal object for laws or defects.

BACKGROUND OF THE INVENTION

Ultrasonic testing of objects to detect subsurface flaws or defects is widely used, particularly in testing the integrity of pipe in power plants which conduct fluid under pressure.

In ultrasonic testing the time measurement between a transmitted pulse and the receipt of a reflected or echo pulse from a non-continuity in the object under test is a measure of distance.

Various modes of propagation of the primary wave may be utilized in ultrasonic testing. A longitudinal wave generally referred to as L-wave is a compressional wave along a given axis.

A shear or transverse wave is one which tends to move molecules of the piece under test in a direction perpendicular to the direction of the wave without changing the volume of the molecules. Ultrasonic testing may be practiced using either wave mode or converted wave modes. Sometimes surface waves are utilized as described in U.S. Pat. Nos. 5,085,082 and 4,658,649. Those mentioned patents may be considered to be representative of some known testing techniques.

Current ultrasonic methods for detection, analysis, and sizing of surface connected planar flaws typically use several techniques. Each technique requires different calibration techniques, calibration standards, transducers, and modes of propagation. Data is recorded from each technique and analyzed to determine flaw characteristics and size. These techniques when properly applied by skilled technicians can be effective.

However, the reliability of this approach has not been good. This has led the ASME (American Society of Mechanical Engineers) Section XI standard committee to publish Appendix VIII to ASME XI. ASME Section XI is the governing document for inservice inspection of nuclear power plant components. This document, upon approval by the Nuclear Regulatory Commission, will require that all ultrasonic examinations performed to ASME XI be performed with procedures that have been proven by demonstration and by examiners who have qualified by examination.

The reason for the unreliability of the current approach is generally considered to be inadequate training of examiners in all of the techniques which are available to them. However, the complexity of these techniques, and the variations in their effectiveness under different conditions on a variety of components makes it virtually impossible to greatly improve reliability. In addition, the complexity of the varied techniques results in inconsistent conclusions between examiners.

In addition to being generally unreliable, the current approach is time consuming and expensive. The direct expense results from the time it takes to perform the several techniques and all of the associated equipment which is required. Some other costs which are harder to measure directly include the following:

Cost of training examiners in several techniques.

Cost of radiation dose to the examiners, and the additional examiners needed due to the dose limits for each examiner.

Cost of incorrect interpretation of results which may result in unnecessary repairs or unplanned down time due to failure of critical components.

Cost of overchecking examination results.

This invention successfully alleviates the problems discussed above. The technique uses only one operation to perform all the tasks discussed above. Detection, analysis and sizing are all performed simultaneously with the same calibration, equipment, and technique. Not only does this reduce examination time and expense, it also increases examination reliability and consistency. Since only one technique is used, examiner training time is decreased. Examiners can become very proficient with only one technique to learn and practice.

This invention provides an ultrasonic examination technique which is able to detect, analyze, and determine length and through wall extent of planar flaws connected to the surface opposite that from which the ultrasound is propagated. Detection, analysis, and sizing is all done in one single operation.

In view of the known ultrasonic testing techniques the present invention provides a new and improved method of testing for flaws utilizing ultrasonic energy which has a broad range of applicability for various metals for both length and depth sizing of flaws. A method embodying the invention is easy to learn and implement, requires few calibrations, reduces inspection time including calibration and scanning times, and a technician may become qualified in a short period of time.

An object of this invention is to provide a new and improved method of ultrasonic testing.

Another object of this invention is to provide a new and improved ultrasonic testing technique for detection characterization and sizing of flaws connected to the surface of an object opposite that from which the ultrasonic energy is propagated.

A further object of this invention is to provide a new and improved method of ultrasonic testing of welds and base materials in the vicinity of welds which is quickly learned and reduces test time.

A further object of this invention is to provide a new and improved method of ultrasonic testing in the vicinity of a weld in which the piece may be inspected from only one side of the weld.

A further object of this invention is to provide a new and improved ultrasonic testing technique using only a single transducer and which provides direct readings of flaw length and depth, using a single set-up and scanning technique.

A still further object of this invention is to provide a new and improved method of ultrasonic testing in which flaw detection, analysis and sizing are all done in a single operation, and which requires only one set-up.

SUMMARY OF THE INVENTION

The invention comprises providing an L-wave transducer transmitting at an angle of sixty-five to seventy-five degrees (from the vertical) together with associated equipment which is calibrated to provide a linear depth display to approximately two times the thickness of the piece to be inspected. For thinner materials (less than about one-half inch), the point of exit of the center or axis of the transmitted ultrasonic wave from the transducer housing from the leading edge thereof is held to a minimum dimension to facilitate the approach of the transducer to a weld.

To perform a test of a weld or in the vicinity of a weld, the root of a weld is first located using a zero degree test method. This establishes the center line of the weld and serves as a reference position. This reference position is then utilized to determine other positions for the transducer so that the envelopes of the transmitted ultrasonic pulses from the various positions will define an essentially continuous dimension on the under surface of the piece under test. This dimension will longitudinally span the length of the area of the test piece under consideration.

In testing, the transducer is preferably first placed on a first determined position with the axis of the pulses to be transmitted aimed at the root of the weld. The transducer is then moved, parallel to the weld, in the same longitudinal position with respect to the reference position. If a flaw is detected on the oscilloscope, the depth can be displayed and its longitudinal position can be determined. By continuing the parallel movement of the transducer, the length of the flaw cross-wise of ultrasonic scan is determined. The length of the flaw at the opposite surface is determined by first moving the transducer longitudinally until the reflected wave on the oscilloscope is at the full thickness of the piece under test. Then parallel scanning is done at that longitudinal position until the flaw reflection amplitude drops to the noise level. This point is one end of the flaw. The other end of the flaw is determined in a similar manner.

The transducer is then longitudinally advanced toward the flaw for through wall sizing. If and when a flaw tip reflection is detected, the examiner will know the end of the flaw has been detected and will note the depth. If the tip is not detected the examiner will then continue to advance the transducer toward the flaw until the amplitude of the reflection commences to drop. This will indicate that the tip of the flaw is beneath the envelope of the transmitted pulses. This procedure is repeated for each detected flaw.

This technique is single operation, multi-task, non-destructive testing for defect detection, analysis and sizing. The technique utilizes the same angle, mode of propagation, calibration, set-up, and scanning patterns, for all materials, thickness of materials, and configuration of components for which it is applicable. The technique is used to detect, analyze and size planar flaws, such as fatigue cracks, which are connected to the surface opposite that from which the ultrasound is propagated.

The technique relies on the fact that specular reflections received from flaws that have penetration into materials will return to the transducer before reflections which are associated with geometric features of the surface to which the flaw is connected. It also relies on the properties of the longitudinal mode of sound propagation at a sixty-five to seventy-five degree angle. At this range of angles the longitudinal mode loses energy to other modes of propagation when incident on surfaces. This results in reduced specular reflections from opposite wall geometric reflectors such as weld roots and counterbores. These properties increase inspection reliability as only reflections which arrive in time before those from the opposite surface require analysis, and further by reducing the number of nonrelevant reflections from that surface.

Another favorable property of the specified angular range of the longitudinal mode is that a long distance in the direction of ultrasound propagation is effectively examined at each scan location. Scan patterns, which take full advantage of this property, can be determined prior to examination. Hence, scanning time can be reduced while still achieving increased reliability.

With a properly calibrated resolving instrument, such as an oscilloscope, the actual location of reflections can be ascertained. The technique specifies analysis steps to determine if the reflection is from a surface connected flaw. If it is surface connected, its orientation, its length and its through wall extent can be determined with no further set-up steps. All that is required are a few simple steps with the same equipment and calibration technique.

For determination of through wall extent, the tip diffracted pulse or the echo dynamic pattern and amplitude response may be used. Other favorable attributes of the specified angle longitudinal mode are that it provides excellent flaw tip response and it has a long echo dynamic pattern. These attributes provide for the opportunity to accurately determine flaw depth.

All information required for through wall sizing is gathered from the sound beam response before it reaches the surface to which the flaw is connected. Hence, flaws with orientation other than normal to the sound entry surface and flaws connected to surfaces which are not parallel to the sound entry surface can be as accurately sized as flaws oriented to the normal and connected to a parallel surface.

Materials are effectively examined for detection of surface connected planar flaws with minimal scanning time and increased reliability. Using the same equipment and set-up as for detection, any flaws which are found can be classified and sized for length and through wall extent concurrent with the detection examination.

The features of the invention which are believed to be novel are particularly pointed out and distinctly claimed in the claims appended to this specification. The invention, however, together with further objects and advantages thereof may best be appreciated by reference to the following detailed description together with the accompanying drawings.

DETAILED DESCRIPTION OF DRAWINGS

DESCRIPTION OF PREFERRED EMBODIMENT

Figure 1:
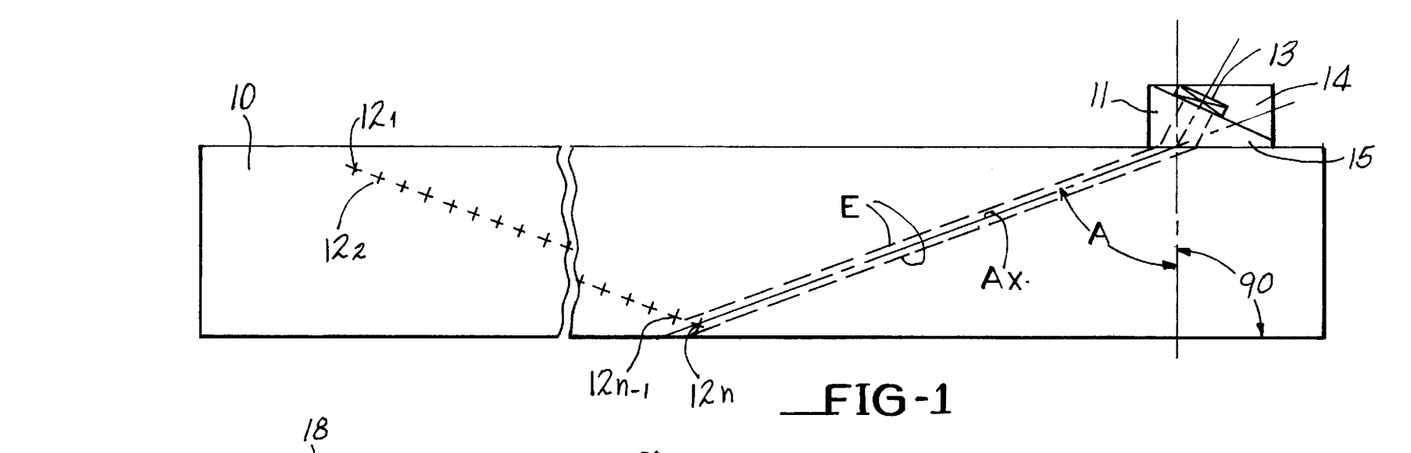
FIG. 1 is a side view of a preferred calibration piece utilized in practice of the invention and also diagrammatically showing an ultrasonic transducer.

FIG. 1 illustrates a calibration piece 10 and a transducer 11 useful in the practice of the invention. The calibration piece has a multiplicity of parallel passages $12_1$ to $12_n$ defined therethrough. The passages are horizontally spaced equidistantly in progression and the passages are also equidistantly spaced vertically.

With the calibration piece the position of reflections from the passages at known depths are set on the oscilloscope of a selected graticule. A linear depth calibration covering approximately two times the thickness to be inspected is the preferred time base set-up.

Block 10 may have calibration marks on its upper surface showing the position for transducer 11 so that the axis of the transmitted ultrasonic beam will detect one of the passages 12 at a known depth.

In the preferred technique, the sensitivity of the test instrument is set by the amplitude of the reflection from the selected passage in calibration block 10 which is at a depth nearest the thickness of the piece to be examined. The amplitude of this reflection is set to approximately one-half of oscilloscope screen peak height.

The transducer 11 comprises two side by side crystals 13 and 13a (only one shown in FIG. 1) which transmit and receive through the hypotenuse or angled surface 14 of a coupling wedge 15.

The wedge surface 14 is so angled that the axis AX of the transmitted beam or pulses enters the calibration piece 10 or a test piece at an angle A, sixty-five to seventy-five degrees, to the vertical. The crystals 13 are cut so as to provide and be most efficient for longitudinal wave (L-wave) transmission and reception, and to minimize or suppress to the extent possible shear or transverse waves.

The range of the specified angles of entrance and propagation of an L-wave into a test piece has been found to be the most efficient for practice of the invention.

As the angle is increased above 75° penetration for detection may be not achieved. As the angle is decreased below 65° one will get more reflections from the geometry of the opposite surface of the test piece, i.e. surface irregularities. This piece may be a pipe with an irregular inside surface, i.e. counterbore or weld root.

Figure 2:
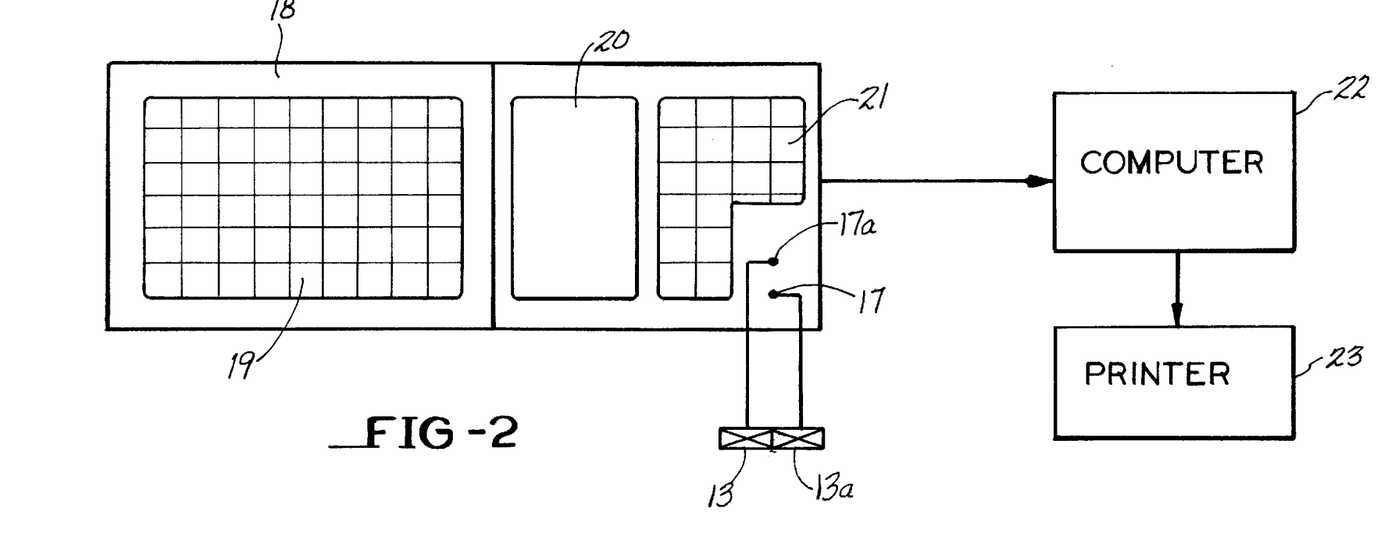
FIG. 2 is a diagram, partially schematic and partially in block form showing apparatus utilized in practicing the invention.

FIG. 2 exemplifies typical apparatus utilized in practicing the invention. The transducer including crystals 13 and 13a are connected to the probe sockets 17 and 17a of an ultrasonic flaw detector 18 which includes an oscilloscope 19, an LCD display 20 and a key pad 21 for entering instructions. A computer 22 may be connected to detector 18 to store and retrieve waveforms, calibrations and flaw data and any other data stored in detector 18 or oscilloscope 19. A suitable detector is a model USK 7D of Krautkrämer Branson of Lewistown, Pa.

Alternately, the computer may be an ultrasonic data acquisition and automated imaging instrument. Such instruments will utilize probes with x-y position encoders and read and store the equivalent of gigabytes of oscilloscope scans (referred to as A-scans), hereinafter exemplified in FIGS. 6a–6c), and may display on a CRT a three dimensional image of a detected flaw. Such instruments will record all pertinent information regarding a detected flaw including location, length and through wall sizing, and flaw characterization. The transducers utilized with such instruments may be as disclosed herein with the addition of x-y position encoders. Position encoders may also be used with transducer 11.

One ultrasonic data acquisition and automated imaging instrument as described above may be one known as "Testpro" by the Infometrics Division (Silver Springs, Md.) of Structural Integrity Associates Corporation of Chicago, Ill. This instrument has probe inputs to which the transducer leads may be directly connected, and instrument 18 not used.

A printer 23 is shown as connected to computer 22 and may print out any data stored therein upon command.

Figure 3:
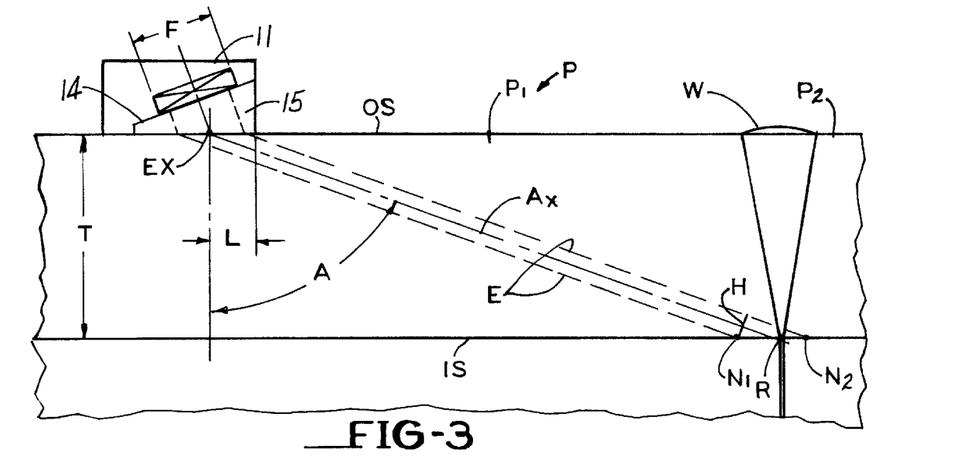
FIG. 3 is a diagrammatic illustration of an ultrasonic transducer specifically designed for use in the invention and further showing the transducer mounted for inspection of a pipe.

Reference is made to FIG. 3 for a description of the transducer 11 and reference characters used in the description of the invention.

Transducer 11 comprises a housing 23 having a wedge 15 of Lucite or suitable material with an inclined surface 14. Crystals 13 and 13a are mounted on surface 14. The wedge surface 14 is so inclined in view of the material to be inspected that the axis AX of the transmitted ultrasonic pulses forms an angle A with the vertical within the specified range.

Transducer 11 is shown on the outside surface OS of a pipe P comprised of pipe sections $P_1$ and $P_2$ joined by a weld W. Transducer 11 has a leading edge 26. The transducer is so constructed that the point EX of entry of the axis AX of the transmitted pulses is a distance L from leading edge 26. The crystal 13 is rectangular and the axis AX emanates from the center thereof at the point EX, which position is marked on the side of the transducer housing for purposes of alignment as hereinafter discussed. The length of crystal 13 is F, and $$L/F \approx 0.5 \qquad (1)$$

This permits a very close approach of the point EX to the convex upper surface of weld W. The thickness of the pipe wall is T and the envelope of the transmitted pulses is identified as E.

The envelope E is shown as collimated for clarity of illustration. In practice, even though the beam is focused, there will be dispersion of the beam.

The dimension H is the height of the envelope E perpendicular to axis AX where the envelope first strikes the inner surface IS at point $N_1$. R is the root of the weld which may extend beyond the surface IS.

The invention is primarily disclosed as used to detect flaws or cracks originating at the inner surface of a test piece primarily disclosed as a pipe and extending through the wall toward the outer or scanning surface. However, use of the invention enables the detection and identification of porosities, voids and other inclusion-like defects. These last mentioned defects are categorized as volumetric defects.

The present invention utilizing the longitudinal wave mode of propagation at an angle of 65° to 75° provides many time saving benefits. The technique of determining the extent of the inspection of the inner surface of a pipe will first be discussed without reference to defects. Then the locating, sizing and characterization of defects is discussed.

Figure 4:
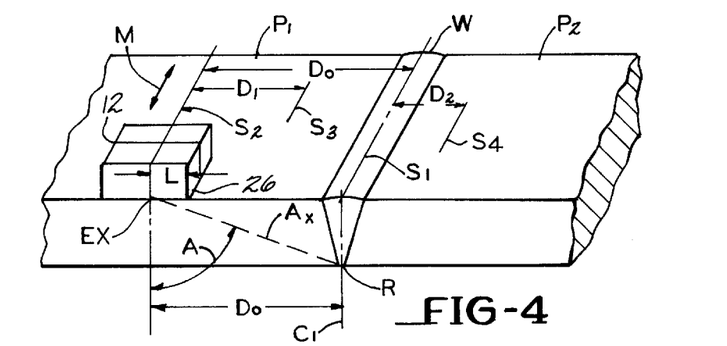
FIG. 4 is a developed plan view in perspective of a section of pipe comprising two butt welded sections with an ultrasonic transducer thereon.

FIG. 4 is an isometric developed view of the two pipe sections $P_1$ and $P_2$ of pipe P joined by butt weld W having root R extending slightly beyond the inside diameter surface IS of the joined pipe.

Figure 4A:
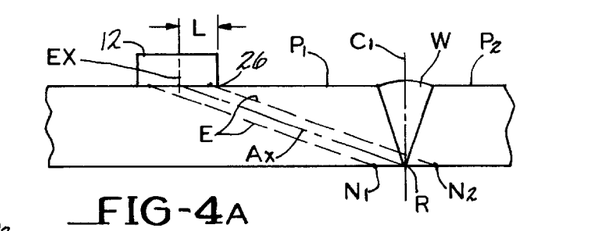
FIGS. 4a–4c are side views of the pipe of FIG. 4 illustrating the positioning of an ultrasonic transducer for scanning for flaws.
Figure 4B:
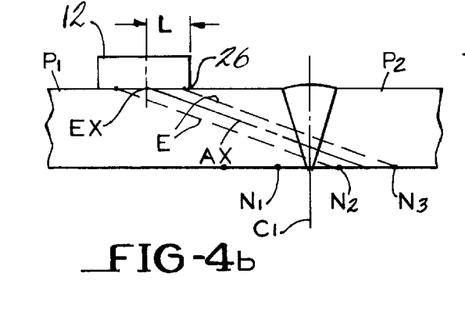
Figure 4C:
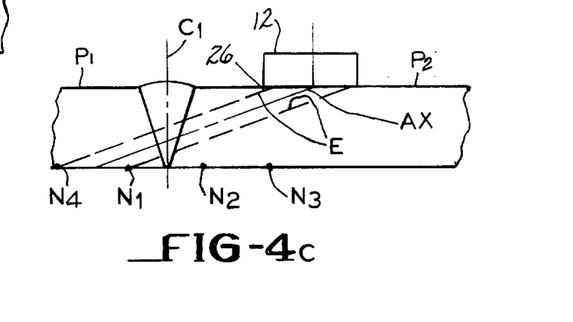

FIGS. 4a–4c are side views of the pipe P, FIG. 4, showing the transducer 11 at various scanning positions on the outer surface of pipe P. It is preferred to scan only from one side of a weld as shown in FIGS. 4a and 4b. FIG. 4c is shown as an alternate position of transducer 12 on the right side of weld W for reasons hereinafter discussed.

The center line $C_1$ of the root is first determined and a scribe mark $S_1$ is made on the outer surface of weld W to indicate the position of root R. The center line $C_1$ is located by use of a zero degree transducer (not shown) which transmits pulsed ultrasonic energy perpendicular to the axis of the pipe. The point of longest time for an echo to return indicates the center line $C_1$. At this point the scribe line $S_1$ is made. Using the zero degree transducer, the wall thickness of the pipe sections may be verified on either side of weld W.

The angle of the axis of the transmitted wave is known in the 65°–75° range. For purposes of discussion this angle A will be considered to be 70° which is a preferred angle.

The point of exit EX of the axis AX of the transmitted pulses from the transducer is marked for visual observation on both sides of the transducer at the distance L from the leading edge 26 of the transducer.

Knowing the location of the weld root R and the angle A it is easy to define a scribe line $S_2$ the distance $D_o$ from root R. The transmitted beam will then have its axis AX aimed at root R and will have a envelope E which encompasses the weld and the interior surface within points $N_1$ and $N_2$.

The points $N_1$ and $N_2$ define a first distance $N_1$–$N_2$ spanning center line $C_1$. on the inside surface IS.

The distance $D_o$ referred to as transducer set-back distance is determined as:

$$D_o = \text{Tan}(A) \cdot T \qquad (2)$$

where

A is the angle of the axis AX of the transmitted beam from the normal.

T is the thickness of the material under test.

Then dimension $D_1$ and scribe line $S_3$ are determined. This determination is approximated by use of the relation $$D_1 = \frac{H}{\cos A} \qquad (3)$$

where H is the vertical height of the envelope E perpendicular to axis AX where the envelope first intersects inner wall IS. See FIG. 3.

H may be determined by measurement on a suitable calibration piece, or using standard beam spread calculations for the material under test. In equation (3), $D_1$ is a close approximation to the maximum permissible distance between transducer scan positions which will result in full coverage of the inner surface in the area of interest. See dimension $N_4$–$N_3$ in FIG. 5c. Additional scan lines or positions should be established to provide the desired area of coverage at inner surface IS.

The scan position lines or scribe lines $S_2$, $S_3$, and $S_4$ (FIG. 4) may be determined by measurement or by use of templates or guides for given wall thicknesses T for a given angle A.

The transducer will later be positioned so that point EX is in alignment with line $S_3$ and the volume within envelope E is scanned as shown in FIG. 4b terminating in the area between points $N_2$ and $N_3$ which define the distance $N_2$–$N_3$.

The directions of lateral or circumferential scan of transducer 11 is shown by the double headed arrow M.

Another position for scan, if necessary, may be made from the opposite side of weld W as shown in FIG. 4c. Here the envelope E intersects surface IS at points $N_1$ and $N_4$ to define the distance $N_4$–$N_1$.

The volume which will be in envelope E will be scanned terminating in the area between points $N_4$ and $N_1$. The scan pattern shown in FIG. 4c is made from scribe line $S_4$ whose position is determined from equation (3) since $N_4$–$N_1$= $N_1$–$N_2$. The dimension of the intersection of envelope E from position $S_4$ is linearly continuously additive to the dimension of envelope from the transducer position $S_2$ on surface IS.

Scanning from scribe position $S_4$ would only be necessary because of space limitations to the left of weld W, as seen in FIGS. 4a–4c, which prevented transducer 11 from being moved to the left a distance greater than $D_o$ to define point $N_4$. It is preferred to scan only from one side of the weld.

In this manner the continuous volume of the pipe wall between points $N_4$ and $N_3$ are scanned for surface IS. The transducer will be moved circumferentially around the pipe at each scan or scribe position substantially parallel to a reference position shown as $S_1$.

FIGS. 4a–4c exemplify the determination of the scan positions in order to totally scan the inside surface IS of pipe P between points $N_4$–$N_3$. If there is a longer area of interest, additional scan positions may be determined trigonometrically as discussed.

The envelopes, as previously pointed out, will disperse. In practice it may be preferred to have the envelopes overlap at the inside surface IS in order to be sure that the totality of the desired length of inside surface IS is scanned. However, as shown, the distances $N_1$–$N_2$, $N_2$–$N_3$ and $N_4$–$N_1$ are essentially completely additive with minimal overlap to cover the total length of inspection, namely $N_4$–$N_3$, with the least number of scanning positions exemplified as $S_2$, $S_3$ and $S_4$.

In cases where the surface of the weld may be ground flush with outside surface OS of pipe P, the first or reference scribe need not be centered on the weld, but in this case it is preferably made in the center of the area of interest. In some cases there may be a space limitation due to a bend in the pipe or a valve on one side of the weld. In such case, only one or possibly no scanning positions may be able to be defined on that side of the weld and a scanning position would be defined with leading edge 26 of the transducer 11 abutting the weld. If necessary, the outer surface of the weld could be ground flush with the outer surface OS of the pipe.

Figure 5A:
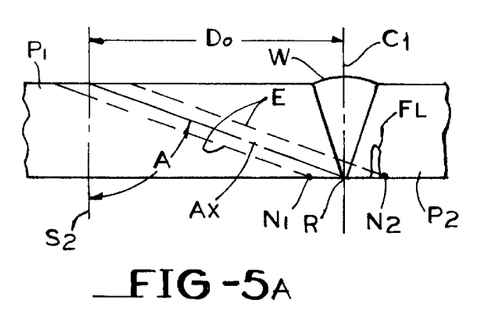
FIGS. 5a–5c are side elevations of a pipe showing the method of identifying internal pipe flaws.
Figure 5B:
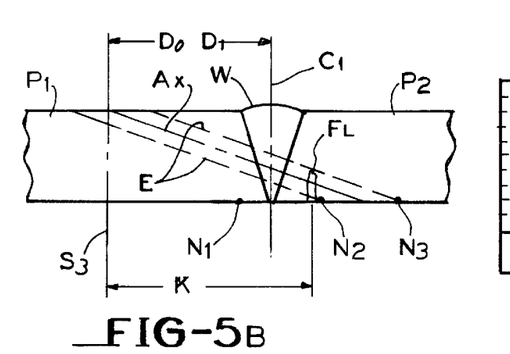
Figure 5C:
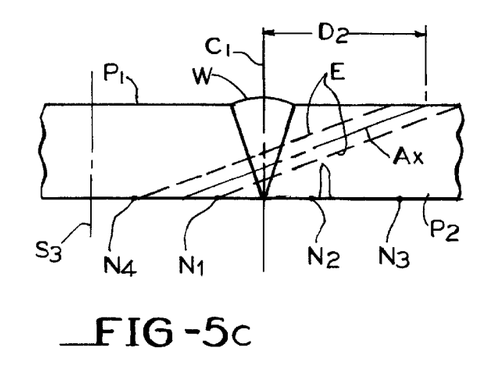
Figure 6A:
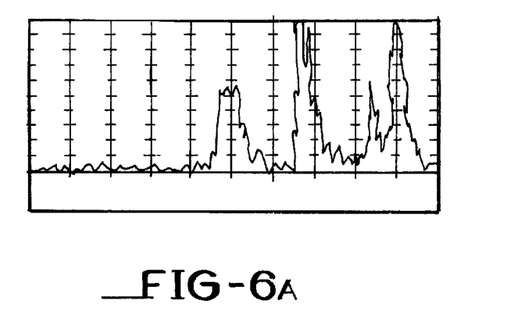
FIGS. 6a–6c are views of the return ultrasonic signals derived from examining as exemplified in FIGS. 5a–5c.
Figure 6B:
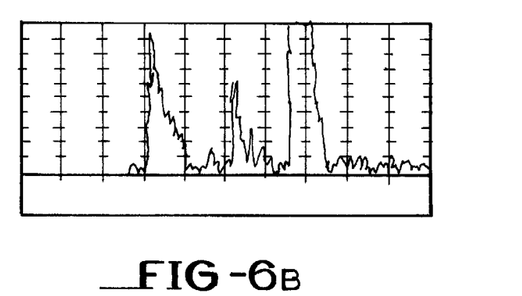
Figure 6C:
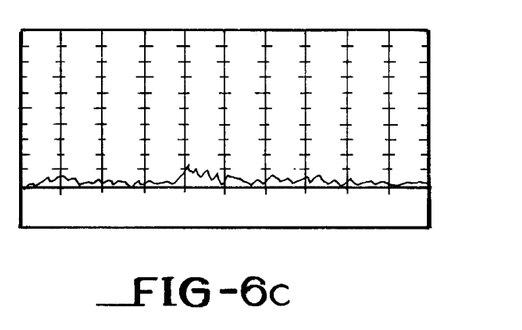

FIGS. 5a–5c illustrate the scanning of a pipe having a planar flaw FL originating from surface IS to the right side of weld W. FIGS. 6a–6c exemplify the reflections which would occur and be seen on oscilloscope 19 for the positions of FIGS. 5a–5c, respectively.

In FIG. 5a the scanning beam is transmitted from the first scan position which is scribe $S_2$ directed at the root of the weld. This scanning beam will detect a portion of flaw FL, as shown at the fifth graticule in FIG. 6a. In FIGS. 6a–6c, the oscilloscopes have been calibrated to twice the thickness T of the pipe wall, thus the first reflected signal is at one-half the X or distance axis of the oscilloscope. All following signals shown in FIG. 6a are ignored. They are not direct longitudinal wave reflections.

Having detected a flaw extending from the inner surface, the examiner may size the flaw laterally to determine its length. The term "length" of the flaw refers to the dimension transverse or substantially perpendicular to the axis of the pipe, and substantially parallel to the weld as determined by a lateral circumferential scan. The examiner will now move the transducer laterally or circumferentially along scribe $S_2$ which is the first scan line, keeping the exit point EX aligned with the scan line. When reflections disappear from the scope as exemplified in FIG. 6c, the examiner will have determined one end of the flaw. The transducer is now moved in the opposite direction with point EX still aligned with scan line $S_2$ until the reflection disappears as shown in FIG. 6c. The examiner will now have determined the length or angular extent of the flaw adjacent inside surface IS. He or an associate will record both the size and the position of the flaw with respect to a scribe line for future reference. Such recording will be stored in memory if a computer or a previously mentioned "Testpro" type instrument is utilized.

While the examiner is moving transducer 11 along scan position $S_2$, he may oscillate it about 15° each way while scanning to have greater visible presence of the flaw.

The examiner may now "walk" the transducer toward the flaw to determine the through wall depth. The term "through wall depth or extent" refers to the dimension of a flaw from the inner surface IS extending toward the scanning surface OS. It may be expressed as a percent of wall thickness T or in dimensional units. Dependent on the thickness of the pipe, the examiner may establish a new scan position where the envelope E does not encompass the tip of the crack and move the transducer laterally in both directions to determine the length or angular extent of the flaw at a given height of envelope E above inside surface IS. The first reflected pulse as shown in FIG. 6a will now appear closer indicating that the envelope E has targeted the flaw at a lesser depth. If the reflection varies from the expected depth in view of the longitudinal position of the transducer, the examiner will know that the flaw is not perpendicular to the surfaces of the pipe and is "leaning" from the perpendicular. With some experience he will be able to determine the direction and extent of "lean".

The examiner will progressively move the transducer through scanning positions (not necessarily at scribe lines) until the tip of a flaw tip reflection signal is observed or there is a noticeable drop in signal amplitude. A flaw tip reflecting signal is a combination of specular reflection and diffraction and will usually have an amplitude as shown in FIG. 6b. In FIG. 5b the envelope E subtends the tip of the flaw at a depth of approximately forty percent of wall thickness T.

This produces a high amplitude of reflected signal as shown in FIG. 6b. FIG. 6b corresponds to the transducer position shown in FIG. 5b. However the flaw tip may not necessarily be resolved at this transducer location.

As shown in FIG. 5b the transducer is positioned at scan line or scribe $S_3$. The transducer may have been moved to this position to begin through wall sizing after the flaw FL was detected at the first scan position and length sized.

After detecting the flaw tip reflection signal, the examiner will move the transducer again longitudinally toward the flaw (if possible) until there is no flaw reflection signal. The examiner has then determined the through wall extent of the flaw. At this point he will move the transducer circumferentially to determine if the through wall extent of the flaw is constant throughout its length, or otherwise determine the length of the flaw at various heights from surface IS. The examiner or an associate will record the sizes and position of the detected flaw. As previously mentioned, this data may be recorded in electronic memory.

After detection of a flaw originating from inner wall IS from one of the determined scanning lines, the examiner may first 1. Move the transducer longitudinally toward the flaw to determine the flaws through wall extent, and then scan circumferentially at different distances from the flaw to determine its length(s), or
2. Upon detection of the flaw first scan circumferentially to determine flaw length and then progressively move longitudinally toward the flaw in steps, scanning circumferentially at each stop for length sizing until he reached a scan position resulting in a flaw tip reflection and then drop in amplitude or no flaw reflection signal.

In either case, the examiner will develop a clear record of the sizing of both the length and through wall extent of the flaw.

After sizing a detected flaw in the area $N_1-N_2$ (FIG. 4a), the examiner will make a complete circumferential scan around scan line $S_2$ to search for other flaws. If other flaws are detected he will examine each flaw in a technique previously described. The examiner will make a record of the length and through wall extent of each detected flaw together with its longitudinal position and angular position with respect to the axis of the pipe P. Alternately such record may be stored in computer memory or the memory of an instrument such as the "Testpro" previously described.

It is possible that in scanning from scan line $S_2$, a flaw will be detected that has a signal reflected indicating that it is not originating at surface IS. This could be a volumetric flaw or a planar flaw originating from surface IS beneath the envelope E. In such case, the examiner would longitudinally back off the transducer from the flaw to determine if it were planar and originating at surface IS. If it is planar and originating at surface IS, he would then make a complete scan as previously described.

The distance K from the point EX to the flaw as initially detected would be determined by $$K = X \cdot \tan A \qquad (4)$$

where X may be read from the depth axis on the oscilloscope.

If the flaw did not originate at surface IS, it wo uld be characterized as volumetric. However, the examiner might still want to size it and determine its position within the pipe wall. This could be done as previously described by longitudinal and circumferential scanning.

After all flaws are detected within the dimension $N_1-N_2$ as shown in FIGS. 4a and 4b, the transducer is positioned on scribe line $S_3$ (FIG. 4) to scan the volume defined by the dimension $N_2-N_3$ as shown in FIG. 5b. At this time flaw FL will be ignored since it has already been positioned, sized and characterized.

In completely sizing flaw FL, it may have been necessary to scan from the right of the weld W as shown in FIG. 5c to develop a oscilloscope pattern as shown in FIG. 6c to verify that the tip of flaw FL did not reach the envelope E when scanning from the right of the weld.

If it is necessary to position transducer 12 at $S_4$ as shown in FIG. 4c and circumferentially moved about the pipe in this position to scan the dimension $N_4-N_1$ around the pipe, any noted defects will be sized for length and through wall extent and recorded as previously described.

However, prior to establishing the scribe line $S_4$, the examiner would move transducer 12 toward weld W from the positions in FIGS. 4b and 5b to determine if the reflection from flaw FL could no longer be discerned to size the through wall extent of flaw FL. If the flaw reflection disappeared from the oscilloscope as transducer 12 approached weld W from the left, the through wall sizing would be accomplished and there would be no need to establish a scanning position defined by scribe line $S_4$. It will be apparent that the dimension $N_4-N_1$ could be established from a scan position to the left of distance $D_o$ (FIG. 4).

FIG. 6a represents an oscilloscope 19 display corresponding to the scan of FIG. 5a and exemplifies a flaw FL reflection originating at surface IS which corresponds to the fifth graticule where the oscilloscope is calibrated to twice the thickness T. The following reflections are of no interest in the practice of the invention.

FIG. 6b represents a display of oscilloscope 19 corresponding to the scan of FIG. 5b and exemplifies a flaw FL tip reflection at the third graticule. This indicates that flaw FL has a through wall size of approximately forty percent of wall thickness T.

FIG. 6c represents a display of oscilloscope 19 corresponding to the scan of FIG. 5c and shows only noise to exemplify that enveloped E is above flaw FL. Substantially the same display (noise only) would eventually be seen if transducer 12 had been walked toward weld W from scribe line $S_3$ from the position shown in FIGS. 4b and 5b.

After scanning to detect, positionally locate and size detected flaws from the predetermined scanning positions (scribe lines), the examiner may make an investigation to characterize volumetric flaws and geometric reflectors which may be ignored as not of interest when scanning for planar flaws. If a flaw is detected an attempt will be made to see if it appears from the opposite side. If it is not found from the opposite side it is a geometric reflector and probably not of interest. If a reflection is found at equal distances from two sides and is at surface IS, it is a planar flaw and will be sized in subsequent scanning. The term "planar" refers to a flaw connected to surface IS. If the reflections from opposite sides do not show a depth equal to the thickness of the piece to be inspected it may be classified as volumetric.

The frequency of the transmitted pulses may be in the range of one to five megahertz. The frequency is not important so long as received signals have adequate resolution. The transducer is selected to have maximum penetration and resolution with minimal beam spread.

The invention provides and is particularly adaptable for scanning the complete volume of a length of interest of a section of a test piece including welds in the test piece and is particularly adaptable to inspection of pipe walls, although not limited thereto. Any length of interest may be completely volumetrically ultrasonically scanned by incrementally establishing scanning positions (scribe lines) which will continuously cover the length of interest.

The invention provides a method for defect detection, sizing and characterization using the same transducer and the same operative steps in one set-up.

The method is independent of the energy of the return pulses and planar flaw orientation since only the first reflected pulse is of interest.

The examiner will require only four transducers for a wide range of wall thicknesses T. Typically, he will use an approximately 0.4" wide by 0.3" high transducer crystal for a thickness of up to 0.5 inch, a 0.6" by 0.57" for dimensions T of 0.5 to 1.5 inch, and a one inch square transducer crystal for dimensions T above 1.5 inch. The fourth transducer will be a zero degree (A=o°) to locate weld root R and to verify dimension T.

The invention utilizes only a single probe and a single calibration technique and provides a direct determination of flaw length and depth, and permits easy characterization of flaws.

It may thus be seen that the objects of the invention set forth above as well as those made apparent are efficiently attained. While a preferred embodiment of the invention has been set forth for purposes of disclosure, other embodiments as well as modifications to the disclosed embodiment may occur to those skilled in the art. Accordingly, the appended claims are intended to cover all embodiments of the invention as well as modification to the disclosed embodiment which do not depart from the spirit and scope of the invention.

What is claimed is:

1. A method of ultrasonically inspecting a selected portion of a metal object having an accessible surface and an opposite surface for flaws using a transducer including an ultrasonic transmitter and receiver where the transducer is moved longitudinally toward and away from said selected portion and laterally essentially parallel to the selected portion, to detect and size flaws in said selected portion and an instrument for recording returned ultrasonic pulse signals received by said receiver where the ultrasonic signals are transmitted in the longitudinal mode within an envelope having a central axis which forms a selected angle with a line perpendicular to a surface of said piece, comprising the steps of a) determining a reference position on said object in the selected portion on the opposite surface thereof, b) determining a first scanning position on said accessible surface of said object for transmitting an envelope of pulses with the axis thereof directed toward said reference position whereby the points where the envelope of transmitted pulses will intersect said opposite surface on either side of said reference position and define a first longitudinal distance between said points, c) positioning said transducer at said first scanning position and moving said transducer on said accessible surface of said object laterally while transmitting ultrasonic signals into said object with the axis of said envelope directed at said reference position, d) noting on said instrument as indicative of a flaw the first reflected pulse of a reflection of said transmitted signals and noting the location thereof, e) positioning said transducer on said accessible surface so as to detect a first indicated flaw and moving said transducer laterally to size the length of said a first indicated flaw, f) moving said transducer longitudinally on said accessible surface to size the through wall extent of said a first indicated flaw g) repeating steps e) and f) for each indicated flaw, and h) recording the position, length and through wall extent of each detected flaw.

2. The method of claim 1 including the further steps of determining one or more additional scanning positions for transmitting ultrasonic signals into said object at the selected angle such that the envelope of pulses transmitted from said one or more additional positions will intersect said opposite surface at points which define one or more longitudinal distances which is essentially a continuation of said first longitudinal distance with minimal overlap of said first and said one or more additional longitudinal distances, whereby said first and said one or more longitudinal distances define on said opposite surface essentially completely additive longitudinal distances which is a continuous length to be inspected and longitudinally encompasses said selected portion, positioning said transducer at each of said one or more scanning positions and moving said transducer laterally while transmitting ultrasonic signals into said object, and repeating steps d), e) f), g) and h) for each determined one or more additional scanning position.

3. The method of claim 1 wherein said positions, lengths and through wall extents are recorded in electronic memory.

4. The method of claim 1 wherein a person performing said moving steps or an associate performs said recording.

5. The method of claim 1 where said selected angle is in the range of sixty-five to seventy-five degrees.

6. The method of claim 2 wherein said determined scanning positions are all on one side of said reference position.

7. The method of claim 2 wherein said determined scanning positions are on both sides of said reference position.

8. The method of claim 1 wherein said instrument is an oscilloscope and said oscilloscope has a distance scale calibrated to a multiple of the thickness of said object.

9. The method of claim 1 where said transducer is oscillated back and forth approximately 15° during step c).

10. A method of inspecting a selected portion of a pipe comprising two sections of butt welded pipe having an outer wall surface and an interior wall surface for flaws using a transducer comprising an ultrasonic transmitter and a receiver and an oscilloscope for displaying received reflected signals where the ultrasonic signals are transmitted by said transmitter in the longitudinal mode within an envelope having a central axis which forms an angle of 65 to 75 degrees with a line perpendicular to the axis of said pipe, comprising the steps of a) determining a reference position on said pipe on the interior surface at the center of said weld, b) determining a scanning position on said outer surface for transmitting an envelope of pulses with the axis thereof directed toward said reference position whereby the envelope of transmitted signals will intersect said interior surface at points on either side of said weld center and define a first longitudinal distance between said points, c) positioning said transducer at said first scanning position and moving said transducer laterally of said pipe axis on said outer surface of said pipe while transmitting ultrasonic signals into said pipe with the axis of said envelope directed at said weld center line, d) noting on said oscilloscope as indicative of a flaw the first reflected pulse of a reflection of said transmitted signals and noting the position thereof, e) positioning said transducer on said outer surface so as to detect a first indicated flaw and moving said transducer laterally of said pipe on the outer surface while transmitting ultrasonic signals to size the length of said a first indicated flaw, f) moving said transducer longitudinally on said outer surface while transmitting ultrasonic signals to size the through wall extent of said a first indicated flaw, g) repeating steps e) and f) for each indicated flaw, and h) recording the position, length and through wall extent of each detected flaw.

11. The method of claim 10, including the further steps of determining one or more additional scanning positions for transmitting ultrasonic signals into said pipe at the selected angle such that the envelope of pulses transmitted from said one or more additional positions will intersect said inner surface at points which define one or more longitudinal distances which is essentially a continuation of said first longitudinal distance with minimal overlap of said first and said one or more additional longitudinal distances, whereby said first and said one or more longitudinal distances define on said inner surface essentially completely additive longitudinal distances which is a continuous length to be inspected and longitudinally encompasses said selected portion, positioning said transducer at each of said one or more scanning positions and moving said transducer laterally while transmitting ultrasonic signals into said object, and repeating steps d), e), f), g) and h) for each determined one or more additional scanning position.

12. The method of claim 10 wherein said positions, sizes and said through wall extents are recorded in electronic memory.

13. The method of claim 10 wherein a person performing said moving steps or an associate performs said recording.

14. The method of claim 11 wherein said determined scanning positions are all on one side of said reference line.

15. The method of claim 11 wherein said determined scanning positions are on both sides of said reference position.

16. The method of claim 10 wherein said instrument is an oscilloscope and has a distance scale calibrated to a multiple of the thickness of the wall of said pipe.

17. The method of claim 10 where said transducer is oscillated back and forth approximately 15° during said step c).

18. A method of inspecting a section of pipe comprising two sections of butt welded pipe having outer and inner surfaces in the vicinity of the weld for the detection of planar flaws connected to said inner surface using a transducer including an ultrasonic signal transmitter and a receiver and an instrument for recording returned ultrasonic signals received by said receiver where the ultrasonic signals are transmitted in the longitudinal mode within an envelope having a central axis which forms a selected angle with the longitudinal axis of said pipe, comprising the steps of a) determining the center of the weld on the inner surface of said pipe, b) determining a scanning position on the outer surface of said pipe for transmitting an envelope of pulse at the selected angle with the axis thereof directed toward said weld center on the inner surface of said pipe whereby the points where the envelope will intersect said inner surface at points on either side of said weld center and define a first longitudinal distance between said points on said inner surface, c) positioning said transducer at said scanning position and moving said transducer on said outer surface laterally of said pipe while transmitting ultrasonic signals into said pipe with the axis of the transmitted envelope directed at said weld center, d) noting on said instrument as indicative of a flaw the first reflected pulse of a reflection of said transmitted signals and noting the location thereof, e) positioning said transducer on said outer surface so as to detect a first indicated flaw and moving the transducer laterally of said pipe longitudinal axis to size the length of said a first indicated flaw, f) moving said transducer longitudinally on said outer surface to determine a connection of said a first indicated flaw to said inner surface and to size the through wall extent of said a first indicated flaw, g) repeating steps e) and f) for each indicated flaw, and h) recording the position, length and through wall extent of each detected flaw.

19. The method of claim 18 wherein said instrument is an oscilloscope having a distance axis which is calibrated to a multiple of the thickness of said pipe.

20. The method of claim 18 wherein said positions, said lengths, and said through wall extents are recorded in electronic memory.

21. The method of claim 18 wherein a person performing said moving steps or an associate performs said recording.

22. The method of claim 18 where said transducer is oscillated back and forth approximately 15° during said step c).

23. The method of claim 18 including the further steps of determining one or more additional scanning positions for transmitting into said pipe at the selected angle such that the envelope of signals transmitted from said one or more additional positions will intersect said inner surface at points which define one or more longitudinal distances which is essentially a continuation of said first longitudinal distance with minimal overlap of said first and said one or more additional longitudinal distances, whereby said first and said one or more longitudinal distances define on said inner surface essentially completely additive longitudinal distances which is a continuous length to be inspected and longitudinally encompasses said weld, and repeating steps c) through h) for each determined one or more additional scanning positions.

24. The method of claim 23 wherein all scanning positions are on one side of said weld.

25. The method of claim 23 wherein said scanning positions are on both sides of said weld.

* * * * *